(12) United States Patent
Keller

(10) Patent No.: US 6,764,512 B2
(45) Date of Patent: Jul. 20, 2004

(54) PLASTIC IMPLANT WITH CHANNEL FOR RADIOGRAPHIC CONTRAST WIRE

(75) Inventor: Arnold Keller, Hamburg (DE)

(73) Assignee: Link Spine Group, Inc., DE (US)

(*) Notice: Subject to any disclaimer, the term of this patent is extended or adjusted under 35 U.S.C. 154(b) by 0 days.

(21) Appl. No.: 09/822,302

(22) Filed: Mar. 29, 2001

(65) Prior Publication Data

US 2001/0027343 A1 Oct. 4, 2001

(30) Foreign Application Priority Data

Apr. 4, 2000 (EP) .............................. 00107331

(51) Int. Cl.$^7$ ................ A61F 2/02; A61F 2/44
(52) U.S. Cl. ................ 623/11.11; 623/17.11; 623/17.16; 600/431
(58) Field of Search ................ 623/1.34, 17.11–17.16; 600/431

(56) References Cited

U.S. PATENT DOCUMENTS

| | | | | |
|---|---|---|---|---|
| RE28,895 E | * | 7/1976 | Noiles | 623/23.22 |
| 4,224,698 A | * | 9/1980 | Hopson | 3/1.912 |
| 4,274,164 A | * | 6/1981 | Rehder et al. | 3/1.913 |
| 4,349,921 A | * | 9/1982 | Kuntz | 3/1 |
| 4,531,243 A | * | 7/1985 | Weber et al. | 623/22 |
| 4,759,766 A | | 7/1988 | Buettner-Janz et al. | |
| 4,883,490 A | * | 11/1989 | Oh | 623/22 |
| 4,892,548 A | * | 1/1990 | Niederer et al. | 623/22 |
| 4,911,718 A | * | 3/1990 | Lee et al. | 623/17 |
| 5,074,881 A | * | 12/1991 | Thull et al. | 623/22 |
| 5,092,897 A | * | 3/1992 | Forte | 623/22 |
| 5,171,281 A | * | 12/1992 | Parsons et al. | 623/17 |
| 5,306,308 A | * | 4/1994 | Gross et al. | 623/17 |
| 5,416,822 A | * | 5/1995 | Kunik | 378/162 |
| 5,423,887 A | * | 6/1995 | Love et al. | 623/2 |
| 5,571,189 A | | 11/1996 | Kuslich | |
| 5,674,294 A | * | 10/1997 | Bainville et al. | 623/17 |
| 5,728,128 A | * | 3/1998 | Crickenberger et al. | 606/97 |
| 5,879,385 A | * | 3/1999 | Crockard et al. | 623/17 |
| 6,001,130 A | * | 12/1999 | Bryan et al. | 623/17 |
| 6,052,625 A | * | 4/2000 | Marshall | 607/122 |
| 6,053,916 A | * | 4/2000 | Moore | 606/61 |
| 6,066,170 A | * | 5/2000 | Lee et al. | 623/5 |
| 6,149,681 A | * | 11/2000 | Houser et al. | 623/1.12 |
| 6,159,241 A | * | 12/2000 | Lee et al. | 623/5.12 |
| 6,261,586 B1 | * | 7/2001 | McKay | 424/423 |
| 6,264,695 B1 | * | 7/2001 | Stoy | 623/17.16 |
| 6,346,123 B1 | * | 2/2002 | McKay | 623/17.11 |
| 6,348,071 B1 | * | 2/2002 | Steffee et al. | 623/17.15 |

FOREIGN PATENT DOCUMENTS

| | | | | |
|---|---|---|---|---|
| EP | 0 392 076 | | 10/1990 | |
| FR | 2 703 580 | | 10/1994 | |
| FR | 2 722 398 A1 | * | 1/1996 | ............. A61F/2/34 |
| WO | 99/62439 | | 12/1999 | |

OTHER PUBLICATIONS

European Search Report for European Application No. 00107331.1.

* cited by examiner

Primary Examiner—David H. Willse
Assistant Examiner—Cheryl Miller

(57) ABSTRACT

A plastic implant having a sliding core, such as an intervertebral endoprosthesis, is formed with a peripheral, preferably circumferential, channel that is configured to receive a radiographic contrast wire. The channel may be partially or fully closed to an outside portion of the sliding core and may include a restriction in the profile of the channel that acts to partially close the channel to the outside portion of the sliding core. The restriction may have a width that is less than the diameter of the radiographic contrast wire. The channel may also include an insertion opening adapted to accept the wire.

19 Claims, 2 Drawing Sheets

PLASTIC IMPLANT WITH CHANNEL FOR RADIOGRAPHIC CONTRAST WIRE

BACKGROUND OF THE INVENTION

1. Field of the Invention

The invention relates to plastic implants with a circumferential channel for receiving a radiographic contrast wire.

2. Description of the Related Art

Plastic implants cannot be clearly imaged in X-rays because of the lack of contrast differentiation between them and the body tissue. In order to check the position of an inserted plastic implant, it is known to provide the latter with a metal wire which is visible in X-rays. For this purpose, a circumferential groove can be worked into the surface of the implant, and the radiographic contrast wire is inserted into this groove. To secure the wire on the implant, the two ends of the wire are usually twisted together. During use of the plastic implant, the wire can become stressed and break. If the wire then migrates from its intended position, it may be necessary to remove it by performing an operation.

To counter the danger of the wire breaking, instead of twisting the ends of the metal wire together, it is known to bend them off and push them into two bores which have been worked perpendicularly into the surface. It has also been attempted to provide one end of the wire with an eyelet and to hook the other end into this eyelet in such a way that a certain play remains. However, the results of these attempts have not been satisfactory.

SUMMARY OF THE INVENTION

It is therefore an object of the invention to make available a plastic implant of the type described, in which the danger of the radiographic contrast wire breaking and/or the danger of the radiographic contrast wire migrating out of position is/are avoided.

For this purpose, the invention provides that the channel receiving the radiographic contrast wire is completely or partially closed off from the outside.

In this way, the wire is held in the channel and is prevented from migrating outwards. Every spatial configuration preventing a wire held in the channel from migrating outwards is included here. The wire ends do not have to be connected to one another. The wire thus forms an open loop which yields with deformations of the implant and is not subjected to any appreciable stresses. For example, upon expansion of the implant, the wire can be adapted to the increased length of the implant circumference by means of sliding along the channel. This applies to the use of an open wire loop and also applies in the case of a break in a closed wire loop.

The term "outwards" relates to the cross-sectional shape of the channel. The course of the channel is not limited to certain shapes. It generally follows the course of the edge. The channel does not have to be closed.

The channel can be closed substantially continuously along its entire length or along most of its length. However, it is generally not a problem if this closure is missing in individual sections of the channel, as long as the sufficiently secure holding of the wire therein is guaranteed. It may even be sufficient to have only a few closed areas distributed about the circumference.

The closure of the channel from the outside does not have to be complete in cross section; instead, partially closed channels are also included here by preference. An only partial closure of the channels from the outside is preferred with a view to permitting production by machine-cutting.

The partial closure of the channel from the outside is preferably obtained by a restriction of its profile, the width of said restriction being less than the wire thickness. To ensure that the wire is clearly positioned, its diameter is advantageously only slightly less than the channel diameter. The wire can be introduced into the channel by, for example, pressing it in from the outside through the restriction. For this purpose, in one possible embodiment, the implant is made elastic in the area of the restriction and the width of the restriction is also dimensioned in such a way that the restriction can be elastically widened for introducing the wire.

However, another embodiment is preferred in which the channel has an insertion opening along a circumference length sufficient for inserting the wire. On the one hand, the insertion opening must have a sufficient length (in the lengthways direction of the channel) to permit easy insertion of the wire into the channel. On the other hand, the insertion opening must not be too long, in order to prevent emergence of the wire in the event of lengthways movements of the wire in the channel. In this respect it is advantageous if both ends of the channel open out in the insertion opening, in particular in alignment with one another, so that a wire end migrating out of one channel opening passes back into the other channel orifice on the opposite side of the insertion opening. In this way, the wire stays trapped within the channel. If the channel is curved, it is advantageous if the wire, in the unstressed and unassembled state, has approximately the same curvature as the channel. If its end migrates out of one channel orifice, then it follows the continuation of this curved path, on which the other channel orifice also lies, so that it is all the easier for it to pass back into this other channel orifice. The term "alignment" in this context is to be understood as meaning that their curved axes coincide.

A sufficient securing of the ends of the wire in the withdrawal opening requires that a wire end migrating out of one channel orifice passes back into the other channel orifice, although this is not absolutely essential; it is instead sufficient if a wire end migrating out of the channel strikes against an opposite wall of the withdrawal opening, thus preventing further movement bringing the wire out of the channel.

Migration of the wire out of the insertion opening can also be prevented by the fact that the wire ends, which in their mounted position each protrude from the channel orifices, are bent away from the channel axis. Displacement of the wire is then limited by means of the contact of the bent ends against the associated channel ends or other walls formed by the insertion opening. In order to provide space for the bent ends, the insertion opening is advantageously widened in relation to the cross section of the channel.

The wires are preferably not bent at the channel ends but instead at a certain distance from said ends, as a result of which a certain play remains for compensating for the above-described changes in length.

In order to limit the friction between the wire and the outer wall of the channel during insertion, it is advantageous if the circumferential channel has a monotone curvature. Areas with a strong curvature are advantageously avoided. To ensure that the wire cannot become jammed in the restriction when being pushed into the channel, the width of the restriction is at most 80%, preferably at most 70% and still more preferably at most 60% of the diameter of the wire. The wire which is to be pushed into the channel is advantageously rounded, at least at its leading end, so that it can be pushed in more easily.

The present invention is particularly advantageous for use in intervertebral endoprostheses with a sliding core made of nonrigid plastic such as polyethylene, in which case it is possible that, as a result of pressure stresses, the sliding core will expand, with enlargement of its circumference.

BRIEF DESCRIPTION OF THE DRAWINGS

The invention is explained below on the basis of an advantageous illustrative embodiment and with reference to the attached drawings, in which.

DETAILED DESCRIPTION OF THE INVENTION

Figure 1:
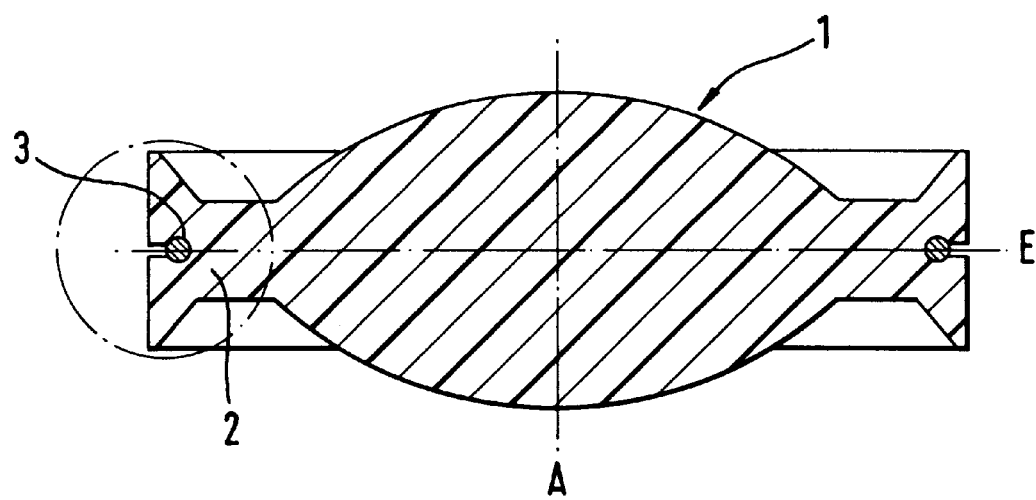
FIG. 1 shows a vertical cross section through the sliding core of an intervertebral endoprosthesis.
Figure 2:
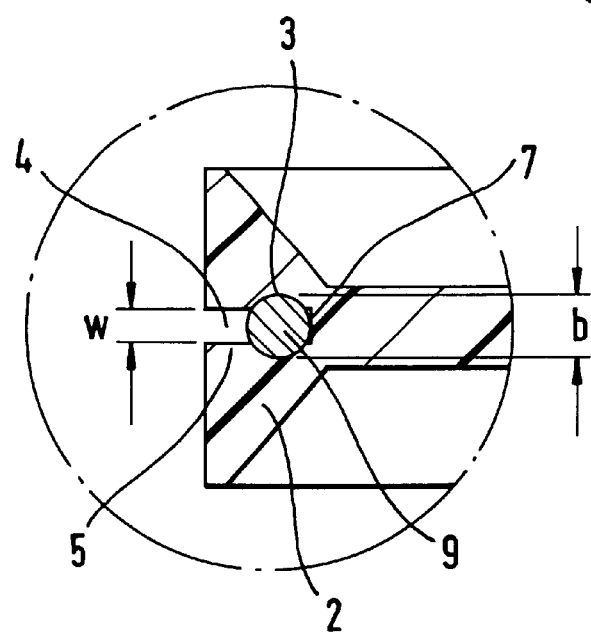
FIG. 2 shows an enlarged detail from FIG. 1, in the area of the channel for the radiographic contrast wire.
Figure 3:
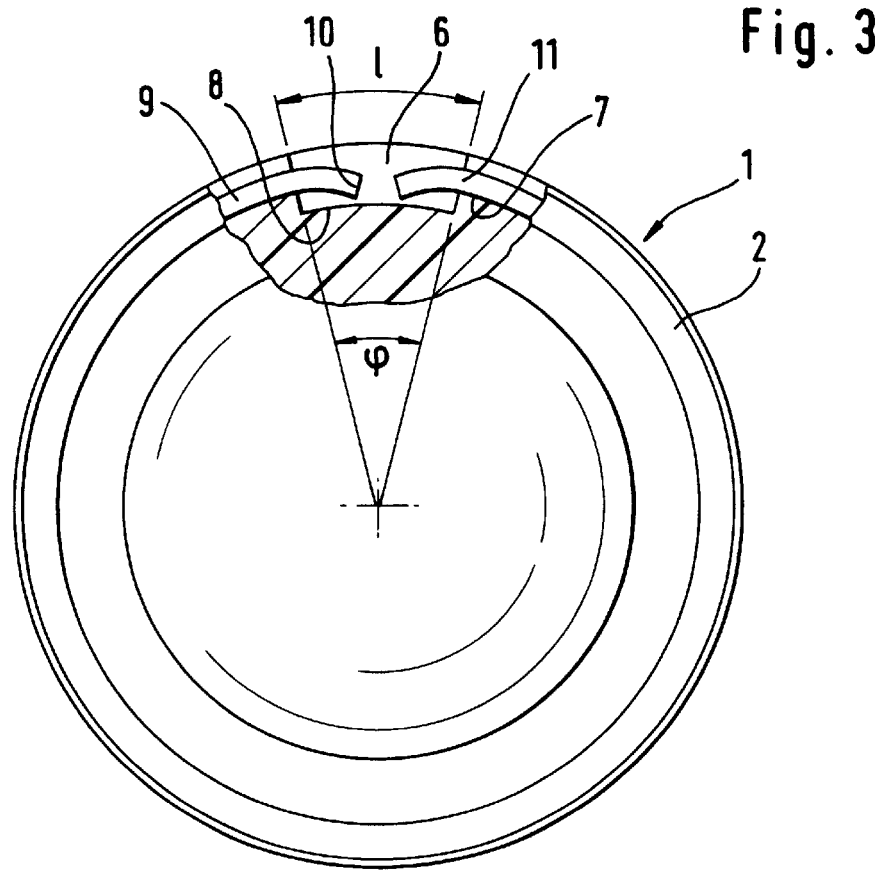
FIG. 3 shows a plan view of the sliding core from FIG. 1, with a horizontal cutout in the area of the insertion opening for the wire.

The sliding core 1 is enclosed above and below by two connection plates (not shown); the intervertebral endoprosthesis thus formed is to be fitted between two vertebrae. The sliding core 1 is substantially discus-shaped with an annular projecting edge 2. In the latter there is a circumferential groove 3, 4 for receiving a radiographic contrast wire 9. As will be seen from FIG. 3, the course of the groove 3, 4 substantially follows the circular edge of the sliding core. The latter is made of nonrigid plastic, in particular polyethylene. A metal wire 9 fitted in the groove 3, 4 is visible on X-rays and makes it possible to check the position of the sliding core 1 and to assess the articulation with the opposite bearing (not shown).

The groove 3, 4 consists of an inner channel 3 and of a profile restriction 4 delimiting the channel towards the outside. The channel 3 is partially closed off from the outside by the restriction 4. The restriction 4 is formed by a slot in the outer channel wall 5, running parallel with the channel 3. The slot width is for example 0.4 mm, while the channel width b is 0.75 mm. The slot width w in relation to the channel width b is thus approximately 50%. This value generally lies in the range from 20 to 80%, preferably 30 to 70%, still more preferably 40 to 60%. In this illustrative embodiment, the slot is used for machine-cutting the channel 3. The wire diameter is 0.7 mm and is thus slightly less than the channel diameter and greater than the slot width.

In an area of the azimuth angle p of preferably 20 to 40°, in the present example 30°, the channel 3 has an insertion opening 6 with a circumference length l of 10 mm. It is generated by means of a cutout in the edge 2 of the prosthesis. In the area of the insertion opening, the slot forming the restriction 4 is widened to the channel width or slightly more. As will be seen from FIG. 3, it is cut in deeper than the channel base 7, so that the base 8 of the insertion opening 6 lies radially further inwards.

Figure 4:
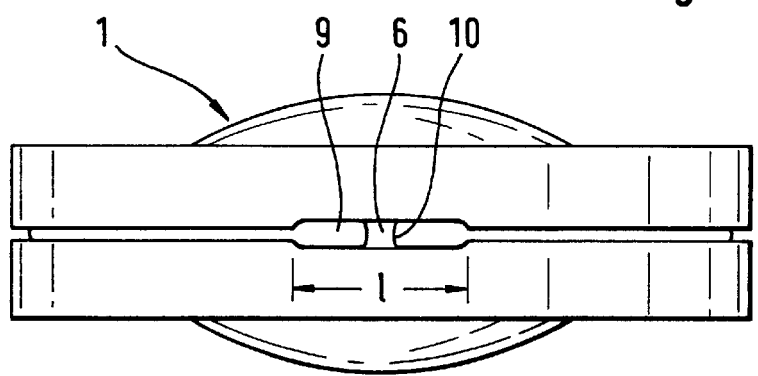
FIG. 4 shows a side view of the sliding core from FIGS. 1 and 2, in the area of the insertion opening.

The length of the radiographic contrast wire 9 used with the sliding core 1 is slightly less than the circumference length of the channel 3. Before it is introduced into the channel 3, the wire is bent into a circle shape roughly corresponding to the course of the channel 3. The wire ends 10 lie freely in the insertion opening. A mutal spacing of the wire ends amounting to several mm is desirable here. Upon assembly, it is pushed into the channel 3 via the insertion opening 6 until it has reached its intended position shown in FIGS. 3 and 4. This is made possible by the rounding or bevelling of the edges at its leading area. After the insertion operation, the ends 10 of the metal wire 9 positioned in the insertion opening 6 are bent inwards, as can be seen from FIG. 3. The bending is so slight or is done at such a distance from the channel orifice 11 that suitable play remains for the length compensation described below. Migration of the wire 9 out of the insertion opening 6 is prevented by means of the bent wire ends 10 striking against the respectively assigned channel orifice or against the opposite walls of the insertion opening 6. Because of the portion of the wire ends 10 protruding beyond the channel orifice 11, these can be gripped and, if appropriate, the wire can be easily removed or replaced.

In order to secure the wire in the implant and to prevent its ends 10 from migrating out of the insertion opening 6, it is not absolutely essential to bend the ends 10 of the wires. If they remain in their originally straight shape or their curved shape adapted to the channel, the shape of the insertion opening prevents them from leaving the implant. If one wire end 10 migrates out of the associated channel orifice 11, then it either passes back into the opposite channel orifice 11, if these openings are in alignment with each other on the channel axis, or this wire end 10 strikes against the wall of the insertion opening which surrounds the opposite channel orifice 11.

As a result of the nonrigid nature of the material, a pressure load on the sliding core 1 along the prosthesis axis A is converted into an expansion in the central plane E extending perpendicular to the axis A. This leads to an increase in the circumference length of the sliding core 1. In the embodiment illustrated, a corresponding length compensation of the open wire loop is achieved by the wire 9, at one or both ends 10, being drawn a corresponding distance into the channel 3. As the pressure on the sliding core 1 decreases, the wire ends 10 are accordingly pushed back out slightly.

What is claimed is:

1. An orthopedic endoprosthesis comprising a plastic part, the plastic part comprising a circumferential surface around a periphery of the plastic part, a channel formed in the plastic part under the circumferential surface, a wall in the plastic part between the channel and the circumferential surface, a slot in the wall forming an insertion opening into the channel and a radiographic contrast wire having ends disposed in the channel through the insertion opening, wherein the slot has a width smaller than a diameter of the radiographic contrast wire, the width of the slot being sized so as to permit pressing the radiographic contrast wire into the channel from the outside of the plastic part due to elastic widening of the slot, the plastic part further comprising a second insertion opening into the channel which is at least as wide as the channel.

2. The orthopedic endoprosthesis of claim 1, wherein the width of the slot is not less than 60% of a diameter of the wire.

3. The orthopedic endoprosthesis of claim 1, wherein the wire is in the form of an open loop.

4. The orthopedic endoprosthesis of claim 1, wherein the slot extends around the entirety of the circumferential surface.

5. The orthopedic endoprosthesis of claim 1, wherein the plastic part is configured to be movable relative to another portion of the orthopedic endoprosthesis.

6. The orthopedic endoprosthesis of claim 1, wherein the channel has a monotone curvature.

7. The orthopedic endoprosthesis of claim 1, wherein edges of the wire are rounded or beveled at least at one end of the wire.

8. The orthopedic endoprosthesis of claim 1, wherein the second insertion opening comprises channel orifices in alignment with one another.

9. The orthopedic endoprosthesis of claim 1, wherein the second insertion opening has a contact wall on a side facing a channel orifice for a wire end emerging from the channel orifice.

10. The orthopedic endoprosthesis of claim 1, wherein the second insertion opening is wider than the channel and at least one end of the wire is bent off in the insertion opening.

11. An orthopedic endoprosthesis comprising a plastic part,
the plastic part comprising a circumferential surface around a periphery of the plastic part, a channel formed in the plastic part under the circumferential surface, a wall in the plastic part between the channel and the circumferential surface having an insertion opening into the channel, a radiographic contrast wire having ends disposed in the channel through the insertion opening and a slot in the wall having a slot width smaller than a diameter of the radiographic contrast wire, wherein the insertion opening is at least as wide as the channel in the plastic part.

12. The orthopedic endoprosthesis of claim 11, wherein the wire is in the form of an open loop.

13. The orthopedic endoprosthesis of claim 11, wherein the channel has a monotone curvature.

14. The orthopedic endoprosthesis of claim 11, wherein edges of the wire are rounded or beveled at least at one end of the wire.

15. The orthopedic endoprosthesis of claim 11, wherein the insertion opening forms channel orifices in alignment with one another.

16. The orthopedic endoprosthesis of claim 11, wherein the insertion opening has a contact wall on a side facing a channel orifice for the wire end emerging from the channel orifice.

17. The orthopedic endoprosthesis of claim 11, wherein at least one end of the wire is bent off in the insertion opening.

18. The orthopedic endoprosthesis of claim 11, wherein the plastic part is configured to be movable relative to another portion of the orthopedic endoprosthesis.

19. The orthopedic endoprosthesis of claim 11, wherein the slot width is sized so as to permit pressing the radiographic contrast wire into the channel from the outside of the plastic part due to elastic widening of the slot.

* * * * *